(12) United States Patent
Andree et al.

(10) Patent No.: US 6,649,760 B2
(45) Date of Patent: Nov. 18, 2003

(54) SUBSTITUTED PHENYLURACILS

(75) Inventors: Roland Andree, Langenfeld (DE); Hans-Georg Schwarz, Langenfeld (DE); Karl-Heinz Linker, Leverkusen (DE); Mark Wilhelm Drewes, Langenfeld (DE); Peter Dahmen, Neuss (DE); Dieter Feucht, Monheim (DE); Rolf Pontzen, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/019,842

(22) PCT Filed: Mar. 23, 2001

(86) PCT No.: PCT/EP01/03332
§ 371 (c)(1),
(2), (4) Date: Feb. 20, 2002

(87) PCT Pub. No.: WO01/77084
PCT Pub. Date: Oct. 18, 2001

(65) Prior Publication Data
US 2002/0173425 A1 Nov. 21, 2002

(30) Foreign Application Priority Data
Apr. 5, 2000 (DE) .......................................... 100 16 893

(51) Int. Cl.⁷ ............................................. C07D 239/54
(52) U.S. Cl. ................ 544/310; 544/311; 544/312; 544/313; 544/314; 544/295; 544/296; 544/28; 544/180
(58) Field of Search ........................... 544/310, 311, 544/312, 313, 314, 295, 296, 180, 284

(56) References Cited

U.S. PATENT DOCUMENTS

| | | | |
|---|---|---|---|
| 4,677,117 A | 6/1987 | Böger | 514/346 |
| 4,897,486 A | 1/1990 | Böger | 546/300 |
| 4,979,982 A | 12/1990 | Brouwer et al. | 71/92 |
| 5,084,084 A | 1/1992 | Satow et al. | 71/92 |
| 5,127,935 A | 7/1992 | Satow et al. | 71/92 |
| 5,154,755 A | 10/1992 | Satow et al. | 71/92 |
| 5,169,430 A | 12/1992 | Strunk et al. | 71/92 |
| 5,183,492 A | 2/1993 | Suchy et al. | 504/243 |
| 5,356,863 A | 10/1994 | Satow et al. | 504/243 |
| 5,416,102 A | 5/1995 | Barnett et al. | 514/351 |
| 5,593,945 A | 1/1997 | Andree et al. | 504/243 |
| 5,681,794 A | 10/1997 | Andree et al. | 504/243 |
| 6,110,870 A | 8/2000 | Andree et al. | 504/243 |
| 6,121,201 A | 9/2000 | Pulman et al. | 504/230 |
| 6,245,715 B1 | 6/2001 | Drewes et al. | 504/243 |
| 6,333,296 B1 | 12/2001 | Pulman et al. | 504/243 |
| 2002/0161224 A1 | 10/2002 | Pulman et al. | 544/236 |

FOREIGN PATENT DOCUMENTS

| | | |
|---|---|---|
| CA | 2225756 | 1/1997 |
| DE | 32 40 975 | 5/1983 |
| DE | 3337828 | 4/1984 |
| DE | 196 04 229 | 8/1996 |
| EP | 255 047 | 2/1988 |
| EP | 1 122 244 | 8/2001 |
| WO | 98/41093 | 9/1998 |
| WO | 99/21837 | 5/1999 |
| WO | 00/02866 | 1/2000 |

OTHER PUBLICATIONS

J. Heterocycl. Chem. 9, Jun. 1972, pp. 513–522, Albert W. Lutz and Susan Trotto, "Novel 6-(Trifluoromethyl)cytosines and 6-(Trifluoromethyl(uracils".

*Primary Examiner*—John M. Ford
(74) *Attorney, Agent, or Firm*—Richard E. L. Henderson; Raymond J. Harmuth

(57) ABSTRACT

Phenyluracils of the general formula (I)

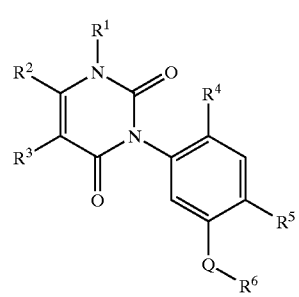

in which
Q, $R^1$, $R^2$, $R^3$, $R^4$, $R^5$ and $R^6$ each have one of the meanings given in the description,
and processes for their preparation and their use as herbicides.

6 Claims, No Drawings

SUBSTITUTED PHENYLURACILS

The invention relates to novel substituted phenyluracils, to processes for their preparation and to their use as crop treatment agents, in particular as herbicides.

It is known that certain substituted phenyluracils have herbicidal properties (cf. EP 408382/U.S. Pat. No. 5,084,084/U.S. Pat. No. 5,127,935/U.S. Pat. No. 5,154,755, EP 563384, EP 648749, U.S. Pat. No. 4,979,982, U.S. Pat. No. 5,169,430, WO 91/00278, WO-A-97/01541, WO-A-00/02866, WO-A-98141093). However, these compounds have hitherto not attained significant importance.

This invention, accordingly, provides the novel substituted phenyluracils of the general formula (I)

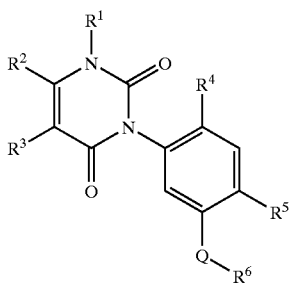

(I)

in which

Q represents O (oxygen), S (sulphur), SO or $SO_2$, $R^1$ represents hydrogen, amino, optionally cyano-, halogen- or $C_1$–$C_4$-alkoxy-substituted alkyl having 1 to 4 carbon atoms or in each case optionally halogen-substituted alkenyl or alkinyl having in each case 2 to 4 carbon atoms, $R^2$ represents cyano, carboxyl, carbamoyl, thiocarbamoyl or in each case optionally cyano-, halogen- or $C_1$–$C_4$-alkoxy-substituted alkyl or alkoxycarbonyl having in each case 1 to 4 carbon atoms, $R^3$ represents hydrogen, halogen or optionally halogen-substituted alkyl having 1 to 4 carbon atoms, $R^4$ represents hydrogen, nitro, cyano or halogen, $R^5$ represents cyano, thiocarbamoyl, bromine or in each case optionally halogen-substituted alkyl or alkoxy having in each case 1 to 4 carbon atoms, and $R^6$ represents an optionally nitro-, hydroxyl-, mercapto-, amino-, cyano-, carboxyl-, carbamoyl-, halogen-, $C_1$–$C_4$-alkyl-, cyano-$C_1$–$C_4$-alkyl-, carboxyl -$C_1$–$C_4$-alkyl-, $C_1$–$C_4$-halogenoalkyl-, $C_1$–$C_4$-alkoxy-$C_1$–$C_4$-alkyl-, $C_1$–$C_4$-alkoxycarbonyl-$C_1$–$C_4$-alkyl-, $C_1$–$C_4$-alkylaminocarbonylalkyl-, di-($C_1$–$C_4$-alkyl)-aminocarbonylalkyl-, $C_1$–$C_4$-alkoxy-, cyano-$C_1$–$C_4$-alkoxy-, $C_1$–$C_4$-halogenoalkoxy-, $C_1$–$C_4$-alkoxy-$C_1$–$C_4$-alkoxy-, carboxyl-$C_1$–$C_4$-alkoxy-, $C_1$–$C_4$-alkoxy-carbonyl-$C_1$–$C_4$-alkoxy-, $C_1$–$C_4$-alkylaminocarbonyl-$C_1$–$C_4$-alkoxy-, di-($C_1$–$C_4$-alkyl)-aminocarbonyl-$C_1$–$C_4$-alkoxy-, $C_1$–$C_4$-alkoxy-carbonyl-, $C_2$–$C_4$-alkenyloxy-, $C_2$–$C_4$-alkinyloxy-, $C_1$–$C_4$-alkylthio-, $C_1$–$C_4$-halogenoalkyl-thio-, $C_1$–$C_4$-alkylsulphinyl-, $C_1$–$C_4$-halogenoalkylsulphinyl-, $C_1$–$C_4$-alkyl-sulphonyl-, $C_1$–$C_4$-halogenoalkylsulphonyl-, $C_1$–$C_4$-alkyl-carbonyl-amino-, $C_1$–$C_4$-alkoxy-carbonyl-amino- or $C_1$–$C_4$-alkyl-sulphonyl-amino-substituted nitrogen-containing heterocyclic grouping from the group consisting of pyrrolyl, pyrazolyl, imidazolyl, triazolyl, triazinyl, pyridinyl, pyrazinyl, pyridazinyl, pyrimidinyl, triazinyl, benzoxazolyl, benzothiazolyl, quinolinyl, quinazolinyl, quinoxalinyl, including all possible tautomeric forms of the compounds of the general formula (I) and the possible salts and acid or base adducts of the compounds of the general formula (I).

In the definitions, the hydrocarbon chains, such as alkyl or alkanediyl, are in each case straight-chain or branched—including in combination with heteroatoms, such as in alkoxy.

Preferred substituents or preferred ranges of the radicals that are present in the formulae given above and below are defined below.

Q preferably represents O (oxygen), S (sulphur) or $SO_2$.

$R^1$ preferably represents hydrogen, amino, in each case optionally cyano-, fluorine-, chlorine-, methoxy- or ethoxy-substituted methyl, ethyl, n- or i-propyl, or in each case optionally fluorine- and/or chlorine-substituted propenyl or propinyl.

$R^2$ preferably represents cyano, carboxyl, carbamoyl, thiocarbamoyl or in each case optionally cyano-, fluorine-, chlorine-, methoxy- or ethoxy-substituted methyl, ethyl, n- or 1-propyl, methoxycarbonyl, ethoxycarbonyl, n- or i-propoxycarbonyl.

$R^3$ preferably represents hydrogen, fluorine, chlorine, bromine or in each case optionally fluorine- and/or chlorine-substituted methyl, ethyl, n- or i-propyl.

$R^4$ preferably represents hydrogen, cyano, fluorine, chlorine or bromine.

$R^5$ preferably represents cyano, thiocarbamoyl, bromine or in each case optionally fluorine- and/or chlorine-substituted methyl, ethyl, methoxy or ethoxy.

$R^6$ preferably represents an in each case optionally nitro-, hydroxyl-, amino-, cyano-, carboxyl-, carbamoyl-, fluorine-, chlorine-, bromine-, methyl-, ethyl-, n- or i-propyl-, n-, i-, s- or t-butyl-, chloromethyl-, fluoromethyl-, dichloromethyl-, difluoromethyl-, trichloromethyl-, trifluoromethyl-, chlorodifluoromethyl-, fluorodichloromethyl-, chloroethyl-, fluoroethyl-, dichloroethyl-, difluoroethyl, chlorofluoroethyl-, trichloroethyl-, trifluoroethyl-, chlorodifluoroethyl-, fluorodichloroethyl-, tetrafluoroethyl-, chlorotrifluoroethyl-, pentafluoroethyl-, chloro-n-propyl-, fluoro-n-propyl-, chloro-i-propyl-, fluoro-i-propyl-, dichloropropyl-, difluoropropyl-, trichloropropyl-, trifluoropropyl-, cyanomethyl-, cyanoethyl-, cyanopropyl-, carboxymethyl-, carboxyethyl-, carboxypropyl-, methoxymethyl-, ethoxymethyl-, propoxymethyl-, methoxyethyl-, ethoxyethyl-, methoxycarbonylmethyl-, ethoxycarbonylmethyl-, n- or i-propoxycarbonylmethyl-, methylaminocarbonylmethyl-, ethylaminocarbonylmethyl-, dimethylaminocarbonylmethyl-, methoxycarbonylethyl-, ethoxycarbonylethyl-, n- or i-propoxycarbonylethyl-, methoxy-, ethoxy-, n- or i-propoxy-, n-, i-, s- or t-butoxy-, difluoromethoxy-, trifluoromethoxy-, chlorodifluoromethoxy-, carboxymethoxy-, carboxyethoxy-, methoxycarbonylmethoxy-, ethoxycarbonylmethoxy-, n- or i-propoxycarbonylmethoxy-, methylaminocarbonylmethoxy-, ethylaminocarbonylmethoxy-, dimethylaminocarbonylmethoxy-, methoxycarbonylethoxy-, ethoxycarbonylethoxy-, n- or i-propoxycarbonylethoxy-, methylaminocarbonylethoxy-, ethylaminocarbonylethoxy-, dimethylaminocarbonylethoxy-, methoxycarbonyl-, ethoxycarbonyl-, n- or i-propoxycarbonyl-, propenyloxy-, butenyloxy-, propinyloxy-, butinyloxy-, methylthio-, ethylthio-, n- or i-propylthio-, n-, i-, s- or t-butylthio-, difluoromethylthio-, trifluoromethylthio-, chlorodifluoromethylthio-, methylsulphinyl-, ethylsulphinyl-, n- or i-propylsulphinyl-, trifluoromethylsulphinyl-, methylsulphonyl-, ethylsulphonyl-, n- or i-propylsulfonyl-, trifluoromethylsulphonyl-, acetylamino-, propionylamino-, n- or i-butyroylamino-, methoxycarbonylamino-, ethoxycarbonylamino-, n- or i-propoxycarbonylamino-, methylsulphonylamino-, ethylsulphonylamino-, n- or i-propylsulphonylamino- substituted nitrogen-containing heterocyclic grouping form the group consisting of pyrrolyl, pyrazolyl, imidazolyl, triazolyl, triazolinyl, pyridinyl, pyrazinyl, pyridazinyl, pyrimidinyl, triazinyl, benzoxazolyl, benzothiazolyl, quinolinyl, quinazolinyl, quinoxalinyl.

Q particularly preferably represents O (oxygen) or S (sulphur).

$R^1$ particularly preferably represents hydrogen, amino or represents in each case optionally fluorine-, chlorine-, methoxy- or ethoxy-substituted methyl or ethyl.

$R^2$ particularly preferably represents cyano, carboxyl, carbamoyl or in each case optionally fluorine- and/or chlorine-substituted methyl, ethyl, methoxycarbonyl or ethoxycarbonyl.

$R^3$ particularly preferably represents hydrogen, fluorine, chlorine, bromine or in each case optionally fluorine- and/or chlorine-substituted methyl or ethyl.

$R^4$ particularly preferably represents hydrogen, fluorine or chlorine.

$R^5$ particularly preferably represents cyano, thiocarbamoyl, bromine or trifluoromethyl.

$R^6$ particularly preferably represents an in each case optionally nitro-, hydroxyl-, amino-, cyano-, carboxyl-, carbamoyl-, fluorine-, chlorine-, bromine-, methyl-, ethyl-, n- or i-propyl-, n-, i-, s- or t-butyl-, dichloromethyl-, difluoromethyl-, trichloromethyl-, trifluoromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, chlorodifluoromethoxy-, carboxymethoxy-, carboxyethoxy-, methoxycarbonylmethoxy-, ethoxycarbonylmethoxy-, n- or i-propoxycarbonylmethoxy-, methoxycarbonylethoxy-, ethoxycarbonylethoxy-, n- or i-propoxycarbonylethoxy-, methoxycarbonyl-, ethoxycarbonyl-, propenyloxy-, butenyloxy-, propinyloxy-, butinyloxy-, methylthio-, ethylthio-, n- or i-propylthio-, n-, i-, s- or t-butylthio-, difluoromethylthio-, trifluoromethylthio-, chlorodifluoromethylthio-, methylsulphinyl-, ethylsulphinyl-, n- or i-propylsulphinyl-, trifluoromethylsulphinyl-, methylsulphonyl, ethylsulphonyl-, n- or i-propylsulphonyl-, trifluoromethylsulphonyl-, acetylamino-, propionylamino-, n- or i-butyroylamino-, methoxycarbonylamino-, ethoxycarbonyl amino-, n- or i-propoxycarbonyl amino-, methylsulphonylamino-, ethylsulphonylamino-, n- or i-propylsulphonylamino- substituted nitrogen-containing heterocyclic grouping from the group consisting of pyrrolyl, pyrazolyl, imidazolyl, triazolyl, triazolinyl, pyridinyl, pyrazinyl, pyridazinyl, pyrimidinyl, triazinyl, benzoxazolyl, benzothiazolyl, quinolinyl, quinazolinyl, quinoxalinyl.

Q very particularly preferably represents O (oxygen).

$R^1$ very particularly preferably represents hydrogen, amino, methyl or ethyl.

$R^2$ very particularly preferably represents cyano or trifluoromethyl.

$R^3$ very particularly preferably represents hydrogen, chlorine or methyl.

$R^5$ very particularly preferably represents cyano, thiocarbamoyl or bromine.

$R^6$ very particularly preferably represents in each case optionally hydroxyl-, amino-, cyano-, carboxyl-, carbamoyl-, fluorine-, chlorine-, bromine-, methyl-, ethyl-, n- or i-propyl-, n-, i-, s- or t-butyl-, dichloromethyl-, difluoromethyl-, trichloromethyl-, trifluoromethyl-, chlorodifluoromethyl-, fluorodichloromethyl-, methoxy-, ethoxy-, n- or i-propoxy-, difluoromethoxy-, trifluoromethoxy-, chlorodifluoromethoxy-, carboxymethoxy-, carboxyethoxy-, methoxycarbonylmethoxy-, ethoxycarbonylmethoxy-, n- or i-propoxycarbonylmethoxy-, methoxycarbonylethoxy-, ethoxycarbonylethoxy-, n- or i-propoxycarbonylethoxy-, methoxycarbonyl-, ethoxycarbonyl-, propenyloxy-, butenyloxy-, propinyloxy-, butinyloxy-, methylthio-, ethylthio-, n- or i-propylthio-, difluoromethylthio-, trifluoromethylthio-, chlorodifluoromethylthio-, methylsulphinyl-, ethylsulphinyl-, n- or i-propylsulphinyl-, trifluoromethylsulphinyl-, methylsulphonyl-, ethylsulphonyl-, n- or i-propylsulfonyl-, trifluoromethylsulphonyl-, acetylamino-, propionylamino-, n- or i-butyroylamino-, methoxycarbonylamino-, ethoxycarbonylamino-, n- or i-propoxycarbonylamino-, methylsulphonylamino-, ethylsulphonylamino-, n- or i-propylsulphonylamino- substituted pyrazolyl, pyridinyl, pyrimidinyl, triazinyl or benzoxazolyl.

$R^1$ most preferably represents hydrogen, amino or methyl.

$R^2$ most preferably represents trifluoromethyl.

$R^5$ most preferably represents cyano or bromine.

$R^6$ most preferably represents in each case optionally hydroxyl-, amino-, cyano-, fluorine-, chlorine-, methyl-, ethyl-, trichloromethyl-, methoxy- or ethoxy-substituted pyrazolyl, pyridinyl, pyrimidinyl or benzoxazolyl.

$R^6$ represents, with extraordinary preference, pyrimidinyl.

A very particularly preferred group are those compounds of the formula (I) in which Q represents O (oxygen), $R^1$ represents methyl, $R^2$ represents trifluoromethyl, $R^3$ represents hydrogen, chlorine or methyl, $R^4$ represents hydrogen, fluorine or chlorine, $R^5$ represents cyano and $R^6$ represents 1-methyl-pyrazol-5-yl, 1,3-dimethyl-pyrazol-5-yl, 1,3,4-trimethylpyrazol-5-yl, 1-methyl-3-trifluoromethyl-pyrazol-5-yl, 1-ethyl-pyrazol-5-yl, 1-ethyl-3-methyl-pyrazol-5-yl, 1-ethyl-3- trifluoromethyl-pyrazol-5-yl, 1-n-propyl-pyrazol-5-yl, 1-n-propyl-3-methyl-pyrazol-5-yl, 1-n-propyl-3-trifluoromethyl-pyrazol-5-yl, 1-i-propyl-pyrazol-5-yl, 1-i-propyl-3-methyl-pyrazol-5-yl, 1-i-propyl-3-trifluoromethyl-pyrazol-5-yl, 1-n-butyl-pyrazol-5-yl, 1-i-butyl-pyrazol-5-yl, 1-s-butyl-pyrazol-5-yl or 1-t-butyl-pyrazol-5-yl.

A further very particularly preferred group are those compounds of the formula (I) in which Q represents O (oxygen), $R^1$ represents methyl, $R^2$ represents trifluoromethyl, $R^3$ represents hydrogen, chlorine or methyl, $R^4$ represents hydrogen, fluorine or chlorine, $R^5$ represents bromine and $R^6$ represents 1-methyl-pyrazol-5-yl, 1,3-dimethyl-pyrazol-5-yl, 1,3,4-trimethylpyrazol-5-yl, 1-methyl-3-trifluoromethyl-pyrazol-5-yl, 1-ethyl-pyrazol-5-yl, 1-ethyl-3-methyl-pyrazol-5-yl, 1-ethyl-3-trifluoromethyl-pyrazol-5-yl, 1-n-propyl-pyrazol-5-yl, 1-n-propyl-3-methyl-pyrazol-5-yl, 1-n-propyl-3-trifluoromethyl-pyrazol-5-yl, 1-i-propyl-pyrazol-5-yl, 1-i-propyl-3-methyl-pyrazol-5-yl, 1-i-propyl-3-trifluoromethyl-pyrazol-5-yl, 1-n-butyl-pyrazol-5-yl, 1-i-butyl-pyrazol-5-yl, 1-s-butyl-pyrazol-5-yl or 1-t-butyl-pyrazol-5-yl.

A further very particularly preferred group are those compounds of the formula (I) in which Q represents O (oxygen), $R^1$ represents amino, $R^2$ represents trifluoromethyl, $R^3$ represents hydrogen, chlorine or methyl, $R^4$ represents hydrogen, fluorine or chlorine, $R^5$ represents cyano and $R^6$ represents 1-methyl-pyrazol-5-yl, 1,3-dimethyl-pyrazol-5-yl, 1,3,4-trimethylpyrazol-5-yl, 1-methyl-3-trifluoromethyl-pyrazol-5-yl, 1-ethyl-pyrazol-5-yl, 1-ethyl-3-methyl-pyrazol-5-yl, 1-ethyl-3-trifluoromethyl-pyrazol-5-yl, 1-n-propyl-pyrazol-5-yl, 1-n-propyl-3-methyl-pyrazol-5-yl, 1-n-propyl-3-trifluoromethyl-pyrazol-5-yl, 1-i-propyl-pyrazol-5-yl, 1-i-propyl-3-methyl-pyrazol-5-yl, 1-i-propyl-3-trifluoromethyl-pyrazol-5-yl, 1-n-butyl-pyrazol-5-yl, 1-i-butyl-pyrazol-5-yl, 1-s-butyl-pyrazol-5-yl or 1-t-butyl-pyrazol-5-yl.

A further very particularly preferred group are those compounds of the formula (I) in which Q represents O (oxygen), $R^1$ represents amino, $R^2$ represents trifluoromethyl, $R^3$ represents hydrogen, chlorine or methyl, $R^4$ represents hydrogen, fluorine or chlorine, $R^5$ represents bromine and $R^6$ represents 1-methyl-pyrazol-5-yl, 1,3-dimethyl-pyrazol-5-yl, 1,3,4-trimethylpyrazol-5-yl, 1-methyl-3-trifluoromethyl-pyrazol-5-yl, 1-ethyl-pyrazol-5-yl, 1-ethyl-3-methyl-pyrazol-5-yl, 1-ethyl-3-trifluoromethyl-pyrazol-5-yl, 1-n-propyl-pyrazol-5-yl, 1-n-propyl-3-methyl-pyrazol-5-yl, 1-n-propyl-3-trifluoromethyl-pyrazol-5-yl, 1-i-propyl-pyrazol-5-yl, 1-i-propyl-3-methyl-pyrazol-5-yl, 1-i-propyl-3-trifluoromethyl-pyrazol-5-yl, 1-n-butyl-pyrazol-5-yl, 1-i-butyl-pyrazol-5-yl, 1-s-butyl-pyrazol-5-yl or 1-t-butyl-pyrazol-5-yl.

A further very particularly preferred group are those compounds of the formula (I) in which Q, $R^1$, $R^2$, $R^3$, $R^4$ and $R^5$ have the meanings given above and $R^6$ represents pyrimidin-2-yl, 5-chloro-pyrimidin-2-yl, 5-fluoro-pyrimidin-2-yl, 4,5-dichloro-pyrimidin-2-yl, 4,5-difluoro-pyrimidin-2-yl, 4-chloro-5-fluoropyrimidin-2-yl, 4-methyl-pyrimidin-2-yl, 4,6-dimethyl-pyrimidin-2-yl, 4-methyl-6-trifluoromethyl-pyrimidin-2-yl, 5-chloro-4,6-dimethyl-pyrimidin-2-yl, 5-fluoro-4,6-dimethyl-pyrimidin-2-yl, 4,5,6-trimethyl-pyrimidin-2-yl, 4-methoxy-6-methyl-pyrimidin-2-yl, 6-difluoromethoxy-4-methyl-pyrimidin-2-yl, 4-methoxy-6-trifluoromethyl-pyrimidin-2-yl, 4,6-dimethoxy-pyrimidin-2-yl, pyrimidin-4-yl, 6-chloro-pyrimidin-4-yl, 5,6-dichloro-pyrimidin-4-yl, 6-chloro-5-fluoro-pyrimidin-4-yl, 6-methyl-pyrimidin-4-yl, 5-chloro-6-methyl-pyrimidin-4-yl, 6-trifluoromethyl-pyrimidin-4-yl, 6-hydroxy-pyrimidin-4-yl, 6-methoxy-pyrimidin-4-yl, 6-methoxycarbonylmethoxy-pyrimidin-4-yl, 6-ethoxycarbonylmethoxy-pyrimidin-4-yl, 6-methoxycarbonylethoxy-pyrimidin-4-yl, 6-ethoxycarbonylethoxy-pyrimidin-4-yl, 6-chloro-5-fluoro-pyrimidin-4-yl, 5-fluoro-4-hydroxy-pyrimin-4-yl or 5-fluoro-6-methoxy-pyrimidin-4-yl.

A further very particularly preferred group are those compounds of the formula (I) in which Q, $R^1$, $R^2$, $R^3$, $R^4$ and $R^5$ have the meanings given above and $R^6$ represents pyridin-2-yl, pyridin-3-yl, pyridin-4-yl, 3-chloro-pyridin-2-yl, 3-fluoro-pyridin-2-yl, 4-chloro-pyridin-2-yl, 4-fluoro-pyridin-2-yl, 5-chloro-pyridin-2-yl, 5-fluoro-pyridin-2-yl, 3,4-dichloro-pyridin-2-yl, 3,5-dichloro-pyridin-2-yl, 3,6-dichloro-pyridin-2-yl, 3,4-difluoro-pyridin-2-yl, 3,5-di-fluoro-pyridin-2-yl, 3,6-difluoro-pyridin-2-yl, 3,5,6-trichloro-pyridin-2-yl, 3,5,6-trifluoro-pyridin-2-yl, 3-cyano-pyridin-2-yl, 4-cyano-pyridin-2-yl, 5-cyano-pyridin-2-yl, 6-cyano-pyridin-2-yl, 3-methyl-pyridin-2-yl, 4-methyl-pyridin-2-yl, 5-methyl-pyridin-2-yl, 6-methyl-pyridin-2-yl, 4-chloro-pyridin-3-yl, 4-fluoro-pyridin-3-yl, 5-chloro-pyridin-3-yl, 5-fluoro-pyridin-3-yl, 6-chloro-pyridin-3-yl, 6-fluoro-pyridin-3-yl, 4,5-dichloro-pyridin-3-yl, 4,5-di-fluoro-pyridin-3-yl, 2-cyano-pyridin-3-yl, 4-cyano-pyridin-3-yl, 5-cyano-pyridin-3-yl, 6-cyano-pyridin-3-yl, 2-methyl-pyridin-3-yl, 4-methyl-pyridin-3-yl, 5-methyl-pyridin-3-yl, 6-methyl-pyridin-3-yl, 2-chloro-pyridin-4-yl, 2-fluoro-pyridin-4-yl, 3-chloro-pyridin-4-yl, 3-fluoro-pyridin-4-yl, 2-cyano-pyridin-4-yl, 3-cyano-pyridin-4-yl, 2-methyl-pyridin-4-yl or 3-methyl-pyridin-4-yl.

A further very particularly preferred group are those compounds of the formula (I) in which Q, $R^1$, $R^2$, $R^3$, $R^4$ and $R^5$ have the meanings given above and $R^6$ represents pyrimidin-2-yl, 5-chloro-pyrimidin-2-yl, 5-fluoro-pyrimidin-2-yl, 4,5-dichloro-pyrimidin-2-yl, 4,5-difluoro-pyrimidin-2-yl, 4-chloro-5-fluoro-pyrimidin-2-yl, 4-methyl-pyrimidin-2-yl, 4,6-dimethyl-pyrimidin-2-yl, 4-methyl-6-trifluoromethyl-pyrimidin-2-yl, 5-chloro-4,6-dimethyl-pyrimidin-2-yl, 5-fluoro-4,6-dimethyl-pyrimidin-2-yl, 4,5,6-trimethyl-pyrimidin-2-yl, 4-methoxy-6-methyl-pyrimidin-2-yl, 6-difluoro-methoxy-4-methyl-pyrimidin-2-yl, 4-methoxy-6-trifluoromethyl-pyrimidin-2-yl, 4,6-dimethoxy-pyrimidin-2-yl.

Preference according to the invention is given to those compounds of the formula (I), which contain a combination of the meanings listed above as being preferred.

Particular preference according to the invention is given to those compounds of the formula (I) which contain a combination of the meanings listed above as being particularly preferred.

Very particular preference according to the invention is given to those compounds of the formula (I) which contain a combination of the meanings listed above as being very particularly preferred.

Most preference according to the invention is given to those compounds of the formula (I) which contain a combination of the meanings listed above as being most preferred.

The abovementioned general or preferred radical definitions apply both to the end products of the formula (I) and, correspondingly, to the starting materials or intermediates required in each case for the preparation. These radical definitions can be combined with one another as desired, i.e. including combinations between the given preferred ranges.

The novel substituted phenyluracils of the general formula (I) have interesting biological properties. In particular, they have strong herbicidal activity.

The novel substituted phenyluracils of the general formula (I) are obtained when (a) phenyluracils of the general formula (II)

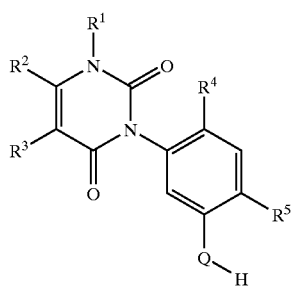

(II)

in which

Q, $R^1$, $R^2$, $R^3$, $R^4$ and $R^5$ are each as defined above are reacted with compounds of the general formula (III)

$X^1$—$R^6$ (III)

in which $R^6$ is as defined above and $X^1$ represents halogen or alkylsulphonyl, if appropriate in the presence of a reaction auxiliary and if appropriate in the presence of a diluent, or when (b) halogenophenyluracils of the general formula (IV)

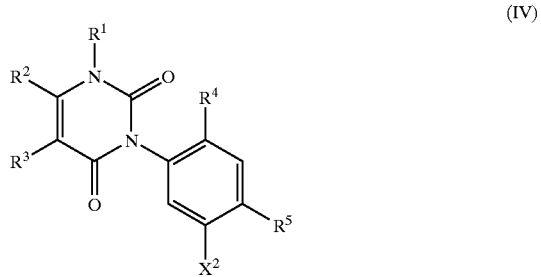

(IV)

in which $R^1$, $R^2$, $R^3$, $R^4$ and $R^5$ are each as defined above and $X^2$ represents halogen, are reacted with compounds of the general formula (V)

M—Q—$R^6$ (V)

in which

Q and $R^6$ are each as defined above and

M represents hydrogen or a metal equivalent, if appropriate in the presence of a reaction auxiliary and if appropriate in the presence of a diluent, or when (c) aminoalkenoic acid esters of the general formula (VI)

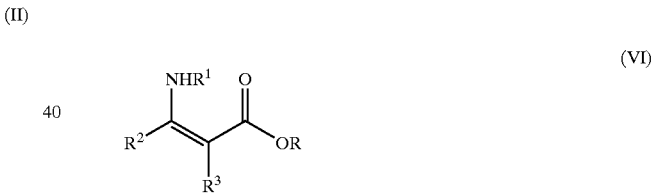

(VI)

in which $R^1$, $R^2$ and $R^3$ are each as defined above and

R represents alkyl, aryl or arylalkyl, are reacted with substituted phenyl isocyanates of the general formula (VII)

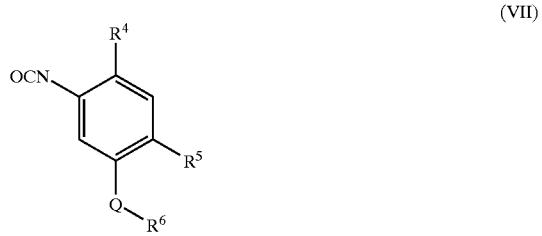

(VII)

in which

Q, $R^4$, $R^5$ and $R^6$ are each as defined above or with substituted phenylurethanes (phenylcarbamates) of the general formula (VIII)

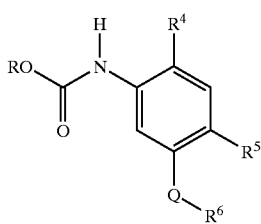

(VIII)

in which

Q, $R^4$, $R^5$ and $R^6$ are each as defined above and

R represents alkyl, aryl or arylalkyl, if appropriate in the presence of a reaction auxiliary and if appropriate in the presence of a diluent, or when (d) substituted N-phenyl-1-alkoxycarbonylamino-maleimides of the general formula (IX)

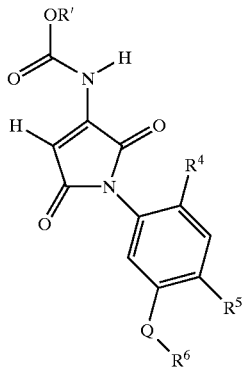

(IX)

in which

Q, $R^4$, $R^5$ and $R^6$ are each as defined above and

R' represents alkyl are reacted with a metal hydroxide in the presence of water and, if appropriate in the presence of an organic solvent, or when (e) substituted phenyluracils of the general formula (Ia)

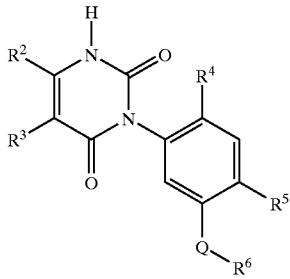

(Ia)

in which

Q, $R^2$, $R^3$, $R^4$, $R^5$ and $R^6$ are each as defined above are reacted with 1-aminooxy-2,4-dinitro-benzene or 2-aminooxysulphonyl-1,3,5-tri-methylbenzene or with alkylating agents of the general formula (X)

$X^3$—$A^1$ (X)

in which $A^1$ represents optionally cyano-, halogen- or $C_1$–$C_4$-alkoxy-substituted alkyl having 1 to 4 carbon atoms or in each case optionally halogen-substituted alkenyl or alkinyl having in each case 2 to 4 carbon atoms, and $X^3$ represents halogen or the grouping —O—$SO_2$—O—$A^1$, if appropriate in the presence of a reaction auxiliary and if appropriate in the presence of a diluent, and electrophilic or nucleophilic and/or oxidation or reduction reactions within the scope of the definition of the substituents are, if appropriate, subsequently carried out in a customary manner.

The compounds of the general formula (I) can be converted by customary methods into other compounds of the general formula (I) in accordance with the above definition, for example by reaction with dicyanogen or hydrogen sulphide (for example $R^5$: Br→CN, CN→$CSNH_2$, cf. the Preparation Examples).

Using, for example, 3-amino-1-(2-chloro-4-bromo-5-hydroxy-phenyl)-4-trifluoro-methyl-3,6-dihydro-2,6-dioxo-1 (2H)-pyrimidine and 4-difluoromethoxy-6-methyl-2-methylsulphonyl-pyrimidine as starting materials, the course of the reaction in the process (a) according to the invention can be illustrated by the following formula scheme:

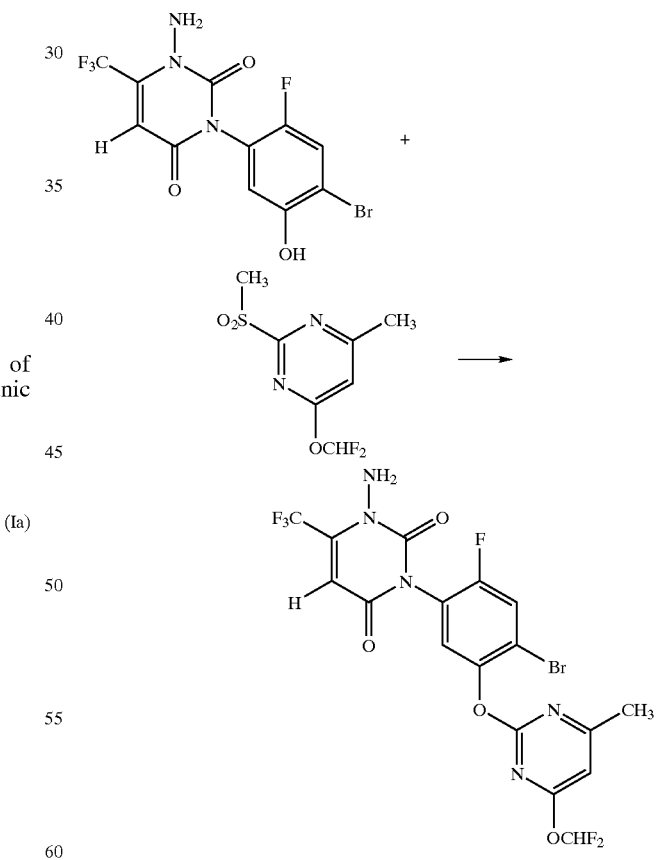

Using, for example, 1-(4-cyano-2,5-difluoro-phenyl)-4-chlorodifluormethyl-3,6-dihydro-2,6-dioxo-1(2H)-pyrimidine and 5-hydroxy-1-methyl-pyrazole as starting materials, the course of the reaction in the process (b) according to the invention can be illustrated by the following formula scheme:

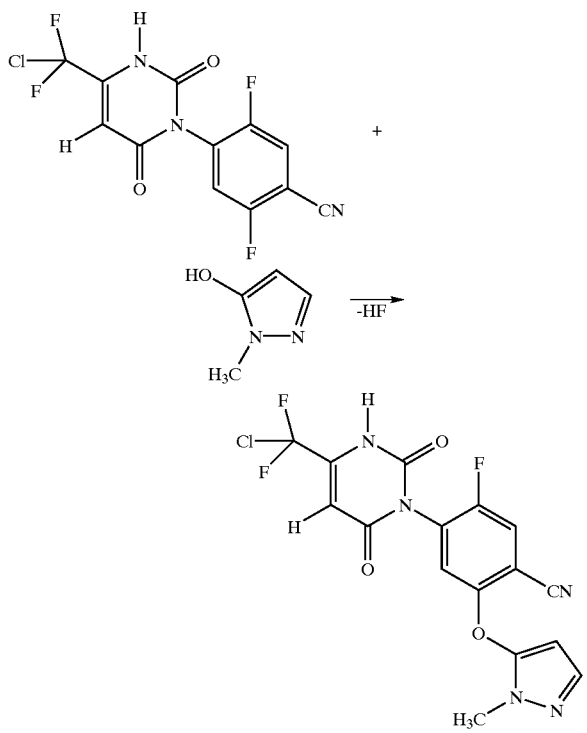

Using, for example, methyl 3-amino-4,4,4-trifluorocrotonate and 4-bromo-2-chloro-5-(5-chloro-pyrimidin-2-yl-thio)-phenyl isocyanate as starting materials, the course of the reaction in the process (c) according to the invention can be illustrated by the following formula scheme:

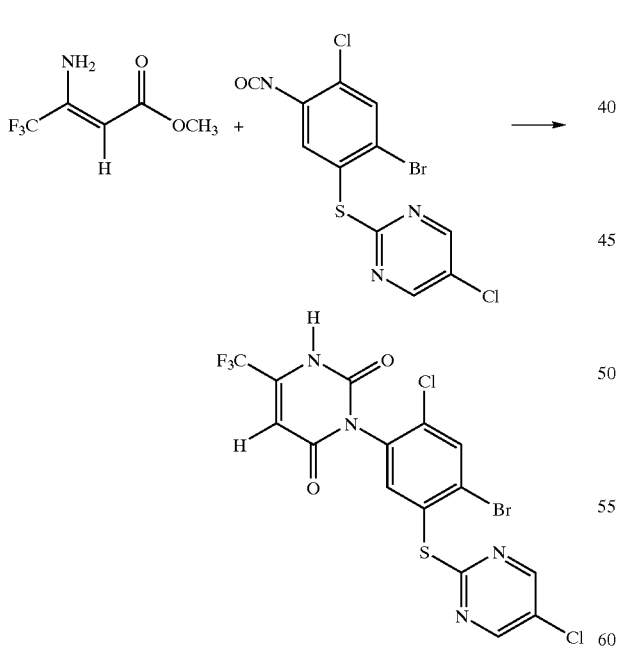

Using, for example, methyl [1-[4-cyano-2-fluoro-5-(pyrimidin-2-yl)-phenyl]-2,5-dioxo-2,5-dihydro-1H-pyrrol-3-yl]-carbamate as starting material, the course of the reaction in the process (d) according to the invention can be illustrated by the following formula scheme:

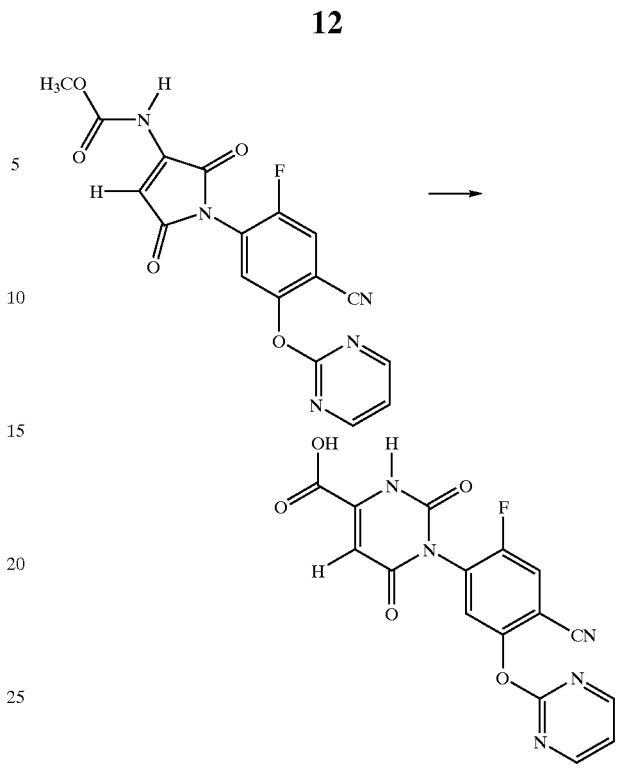

Using, for example, 1-[4-cyano-2-fluoro-5-(1,3-dimethyl-pyrazol-5-yl-oxy)-phenyl]-4-difluoromethyl-3,6-dihydro-2,6-dioxo-1(2H)-pyrimidine and methyl bromide as starting materials, the course of the reaction in the process (e) according to the invention can be illustrated by the following formula scheme:

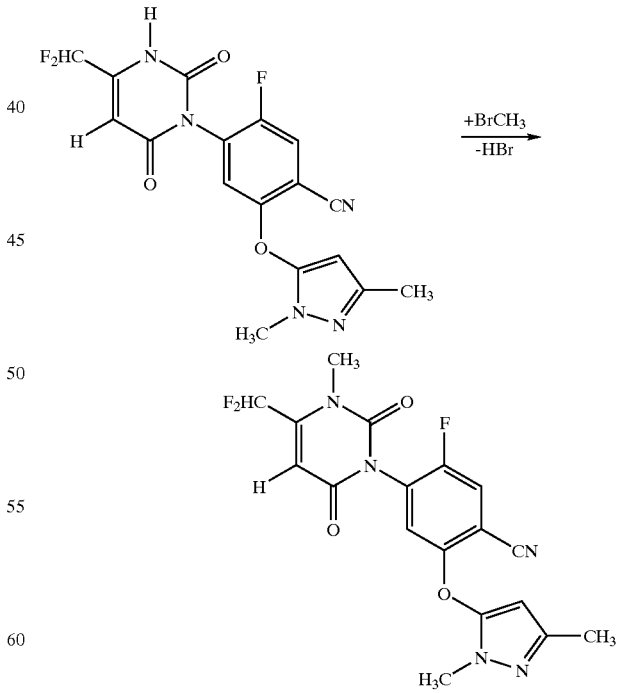

The formula (II) provides a general definition of the phenyluracils to be used as starting materials in the process (a) according to the invention for preparing compounds of the formula (I). In the formula (II), Q, $R^1$, $R^2$, $R^3$, $R^4$ and $R^5$ each preferably or in particular have those meanings which have already mentioned above, in connection with the description of the compounds of the formula (I) according to the invention, as being preferred or as being particularly preferred for Q, $R^1$, $R^2$, $R^3$, $R^4$ and $R^5$.

The starting materials of the general formula (II) are known and/or can be prepared by processes known per se (cf. WO-A-97/01541, WO-A-98/54155).

The formula (III) provides a general definition of the compounds further to be used as starting materials in the process according to the invention. In the general formula (III), $R^6$ preferably has that meaning which has already been mentioned above, in connection with the description of the compounds of the general formula (I) according to the invention, as being preferred, particularly preferred, very particularly preferred or most preferred for $R^6$; $X^1$ preferably represents fluorine, chlorine, bromine, iodine or alkylsulphonyl having 1 to 3 carbon atoms, in particular fluorine, chlorine, bromine or methylsulphonyl.

Most of the starting materials of the general formula (III) are known organic chemicals for synthesis.

The formula (IV) provides a general definition of the halogenophenyluracils to be used as starting materials in the process (d) according to the invention for preparing compounds of the general formula (I). In the general formula (IV), $R^1$, $R^2$, $R^3$, $R^4$ and $R^5$ each preferably have those meanings which have already been mentioned above, in connection with the description of the compounds of the general formula (I) according to the invention, as being preferred, particularly preferred, very particularly preferred or most preferred for $R^1$, $R^2$, $R^3$, $R^4$ and $R^5$; $x^2$ preferably represents fluorine, chlorine or bromine, in particular fluorine or chlorine.

The starting materials of the general formula (IV) are known and/or can be prepared by processes known per se (cf. EP-A-648749).

The formula (V) provides a general definition of the compounds further to be used as starting materials in the process (b) according to the invention. In the general formula (V), Q and $R^6$ each preferably have those meanings which have already been mentioned above, in connection with the description of the compounds of the general formula (I) according to the invention, as being preferred, particularly preferred, very particularly preferred or most preferred for Q and $R^6$; M preferably represents hydrogen or an alkali metal, in particular hydrogen, sodium or potassium.

Most of the starting materials of the general formula (V) are known organic chemicals for synthesis.

The formula (VI) provides a general definition of the aminoalkenoic acid esters to be used as starting materials in the process (c) according to the invention for preparing compounds of the general formula (I). In the general formula (VI), $R^1$, $R^2$ and $R^3$ each preferably have those meanings which have already been mentioned above, in connection with the description of the compounds of the general formula (I) according to the invention, as being preferred, particularly preferred, very particularly preferred or most preferred for $R^1$, $R^2$ and $R^3$; R preferably represents $C_1$–$C_4$-alkyl, phenyl or benzyl, in particular methyl or ethyl.

The starting materials of the general formula (VI) are known and/or can be prepared by processes known per se (cf. J. Heterocycl. Chem. 9 (1972), 513–522).

The formula (VII) provides general definition of the phenyl isocyanates further to be used as starting materials in process (c) according to the invention and the formula (VII) provides a general definition of the phenylurethanes to be used alternatively. In the general formulae (VII) and (VIII), Q, $R^4$, $R^5$ and $R^6$ each preferably have those meanings which have already been mentioned above, in connection with the description of the compounds of the general formula (I) according to the invention, as being preferred, particularly preferred, very particularly preferred or most preferred for Q, $R^4$, $R^5$ and $R^6$; R preferably represents $C_1$–$C_4$-alkyl, phenyl or benzyl, in particular methyl, ethyl, phenyl or benzyl.

The starting materials of the general formulae (VII) and (VIII) have hitherto not been disclosed in the literature; as novel substances, they also form part of the subject-matter of the present application.

The novel substituted phenyl isocyanates of the general formula (VII) are obtained when aniline derivatives of the general formula (XI)

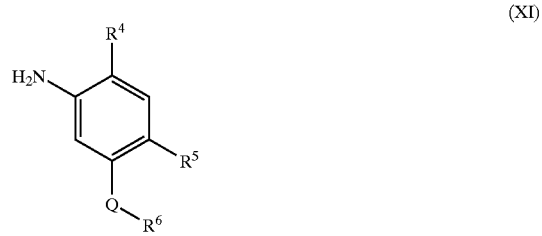

in which
Q, $R^4$, $R^5$ and $R^6$ are each as defined above
are reacted with phosgene in the presence of a diluent, such as, for example, chlorobenzene, at temperatures between –20° C. and +150° C. (cf. also EP-A-648749).

The novel substituted phenylurethanes of the general formula (VIE) are obtained when aniline derivatives of the general formula (XI)

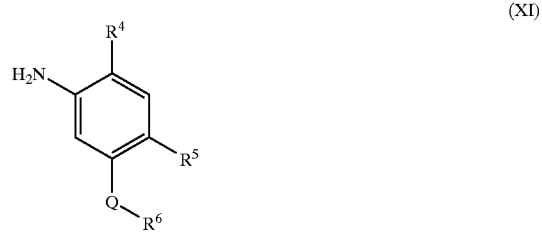

in which
Q, $R^4$, $R^5$ and $R^6$ are each as defined above
are reacted with chlorocarbonyl compounds of the general formula (XII)

in which
R is as defined above,
if appropriate in the presence of an acid acceptor, such as, for example, pyridine, and if appropriate in the presence of a diluent, such as, for example, methylene chloride, at temperatures between –20° C. and +100° C. (cf. the Preparation Examples).

The aniline derivatives of the general formula (XI) required as precursors are generally known and/or can be prepared by processes known per se (cf. DE-A-3240975, DE-A-3337828, EP-A-79311).

Hitherto undisclosed and, as novel substances, part of the subject-matter of the present application are aniline derivatives of the general formula (XIa)

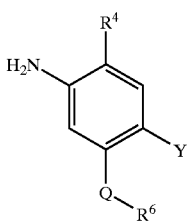

(XIa)

in which

Q, $R^4$ and $R^6$ are each as defined above and

Y represents cyano, thiocarbamoyl or trifluoromethyl.

The novel aniline derivatives of the general formula (XIa) are obtained when (α) anilines of the general formula (XIII)

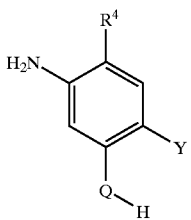

(XIII)

in which

Q, $R^4$ and Y are each as defined above are reacted with compounds of the general formula (III)

 (III)

in which $R^6$ and $X^1$ are each as defined above, if appropriate in the presence of an acid acceptor, such as, for example, potassium hydroxide, potassium carbonate or pyridine, and if appropriate in the presence of a diluent, such as, for example, methanol, acetonitrile, N,N-dimethyl-formamide or N-methyl-pyrrolidone, at temperatures between 0° C. and 200° C. (cf. the Preparation Examples), or when (β) anilines of the general formula (XIV)

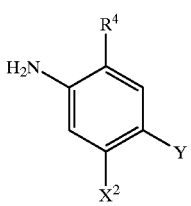

(XIV)

in which $R^4$, $X^2$ and Y are each as defined above are reacted with compounds of the general formula (V)

 (V)

in which

M, Q and $R^6$ are each as defined above, if appropriate in the presence of an acid acceptor, such as, for example, potassium carbonate or sodium hydride, and if appropriate in the presence of a diluent, such as, for example, acetonitrile, N,N-dimethyl-formamide or N-methyl-pyrrolidone, at temperatures between 0° C. and 200° C. (cf. the Preparation Examples).

The formula (IX) provides a general definition of the substituted N-phenyl-1-alkoxycarbonylamino-maleimides to be used as starting materials in the process (d) according to the invention for preparing compounds of the general formula (I). In the general formula (IX), Q, $R^4$, $R^5$ and $R^6$ each preferably have those meanings which have already been mentioned above, in connection with the description of the compounds of the general formula (I) according to the invention, as being preferred, particularly preferred, very particularly preferred or most preferred for Q, $R^4$, $R^5$ and $R^6$; R' preferably represents $C_1$–$C_4$-alkyl, in particular methyl or ethyl.

The novel substituted N-phenyl-1-alkoxycarbonylamino-maleimides of the general formula (IX) are obtained when alkyl (2,5-dioxo-2,5-dihydro-furan-3-yl)-carbamates of the general formula (XV)

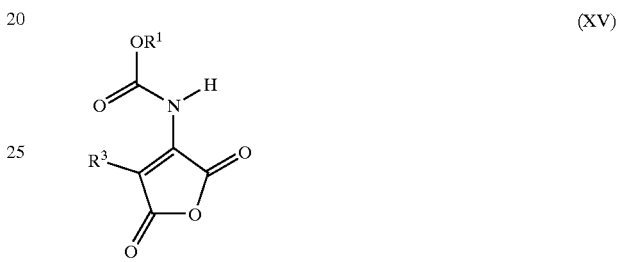

(XV)

in which $R^3$ is as defined above and

R' represents alkyl (in particular methyl or ethyl)

are reacted with aniline derivatives of the general formula (XI)

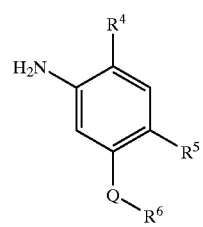

(XI)

in which

Q, $R^4$, $R^5$ and $R^6$ are each as defined above, if appropriate in the presence of a diluent, such as, for example, acetic acid, at temperatures between 0C and 200° C.

The precursors of the general formula (XV) are known and/or can be prepared by processes known per se (cf. DE-A-19604229).

The formula (Ia) provides a general definition of the substituted phenyluracils to be used as starting materials in the process (e) according to the invention for preparing compounds of the general formula (I). In the general formula (Ia), Q, $R^2$, $R^3$, $R^4$, $R^5$ and $R^6$ each preferably or in particular have those meanings which have already been mentioned above, in connection with the description of the compounds of the general formula (I) according to the invention, as being preferred or as being particularly preferred for Q, $R^2$, $R^3$, $R^4$, $R^5$ and $R^6$.

As novel substances, the starting materials of the general formula (Ia) for process (e) also form part of the subject-matter of the present application; they can be prepared by processes (a) to (d) according to the invention.

The formula (X) provides a general definition of the alkylating agents further to be used as starting materials in the process (e) according to the invention. In the general formula (X), $A^1$ preferably represents in each case optionally cyano-, fluorine-, chlorine-, methoxy- or ethoxy-substituted methyl, ethyl, n- or 1-propyl or in each case optionally fluorine- and/or chlorine-substituted propenyl or propinyl, in particular methyl or ethyl; $X^3$ preferably represents chlorine, bromine, iodine, methoxysulphonyloxy or ethoxysulphonyloxy, in particular bromine or methoxysulphonyloxy.

The starting materials of the general formula (X) are known organic chemicals for synthesis.

The processes according to the invention for preparing the compounds of the general formula (I) are preferably carried out using diluents. Suitable diluents for carrying out the processes (a), (b), (c), (d) and (e) according to the invention are, in addition to water, especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methylpyrrolidone or hexamethylphosphoric triamide; esters, such as methyl acetate or ethyl acetate, sulphoxides, such as dimethyl sulphoxide, alcohols, such as methanol, ethanol, n- or 1-propanol, ethylene glycol monomethyl ether, ethylene glycol monoethyl ether, diethylene glycol monomethyl ether, diethylene glycol monoethyl ether, mixtures thereof with water or pure water.

Suitable reaction auxiliaries for the processes (a), (b), (c) and (e) according to the invention are, in general, the customary inorganic or organic bases or acid acceptors. These include preferably alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or 1-propoxide, n-, i-, s- or t-butoxide, or potassium methoxide, ethoxide, n- or i-propoxide, n-, i-, s- or t-butoxide; furthermore also basic organic nitrogen compounds, such as, for example, trimethylamine, triethylamine, tri-propylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo[4.3.0]-non-5-ene (DBN) or 1,8-diazabicyclo[5.4.0]-undec-7-ene (DBU).

Other suitable reaction auxiliaries for the processes (a), (b), (c) and (e) according to the invention are phase-transfer catalysts. Examples of such catalysts which may be mentioned are:

tetrabutylammonium bromide, tetrabutylammonium chloride, tetraoctylammonium chloride, tetrabutylammonium hydrogen sulphate, methyl-trioctylammonium chloride, hexadecyl-trimethylammonium chloride, hexadecyl-trimethylammonium bromide, benzyl-trimethylammonium chloride, benzyl-triethylammonium chloride, benzyl-trimethylammonium hydroxide, benzyl-triethylammonium hydroxide, benzyl-tributylammonium chloride, benzyl-tributylammonium bromide, tetrabutyl-phosphonium bromide, tetrabutylphosphonium chloride, tributyl-hexadecyl-phosphonium bromide, butyl-triphenylphosphonium chloride, ethyl-trioctyl-phosphonium bromide, tetraphenylphosphonium bromide.

Preferred metal hydroxides used in the process (d) according to the invention are alkali metal or alkaline earth metal hydroxides, in particular lithium hydroxide, sodium hydroxide, potassium hydroxide or calcium hydroxide.

When carrying out the processes (a), (b), (c), (d) and (e) according to the invention, the reaction temperatures can be varied within a relatively wide range. In general, the processes are carried out at temperatures between 0C and 150° C., preferably between 10° C. and 120° C.

The processes (a), (b), (c), (d) and (e) according to the invention are generally carried out under atmospheric pressure. However, it is also possible to carry out the processes according to the invention under elevated or reduced pressure—in general between 0.1 bar and 10 bar.

For carrying out the processes according to the invention, the starting materials are generally employed in approximately equimolar amounts. However, it is also possible to use a relatively large excess of one of the components. The reaction is generally carried out in a suitable diluent in the presence of a reaction auxiliary and the reaction mixture is generally stirred at the required temperature for several hours. Work-up is carried out by customary methods (cf. the Preparation Examples).

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: Allium, Ananas, Asparagus, Avena, Hordeum, Oryza, Panicum, Saccharum, Secale, Sorghum, Triticale, Triticum, Zea.

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad activity spectrum when used on the soil or on above-ground parts of plants. To a certain extent, they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diato-maceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use colorants, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 percent by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazon, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenicam, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-)metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop(-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention is illustrated by the examples below.

PREPARATION EXAMPLES

Example 1

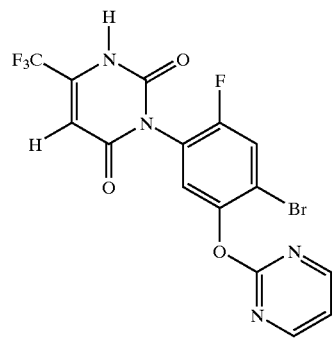

Process (c)

1.03 g (5.6 mmol) of methyl 3-amino-4,4,4-trifluorocrotonate are added to a mixture, cooled to 0° C., of 0.28 g (7 mmol) of sodium hydride (60% strength dispersion in mineral oil) in 10 ml of N,N-dimethyl-formamide. With stirring, the mixture is allowed to warm to room temperature (about 20° C.), and a solution of 2.0 g (5.62 mol) of O-ethyl N-[4-bromo-2-fluoro-5-(pyrimidin-2-yl-oxy)-phenyl]-carbamate in 25 ml of N,N-dimethyl-formamide is then added dropwise. The reaction mixture is heated at 150° C. for 6 hours. The mixture is then poured into 300 ml of 2N hydrochloric acid, approximately the same volume of a 1:1 mixture of diethyl ether and petroleum ether is added and the mixture is stirred for about 3 hours. The resulting crystalline product is isolated by filtration with suction.

This gives 1.6 g (64% of theory) of 1-[4-bromo-2-fluoro-5-(pyrimidin-2-yl-oxy)-phenyl]-4-trifluoromethyl-3,6-dihydro-2,6-dioxo-1 (2H)-pyrimidine.

log P=1.96[a)]

Example 2

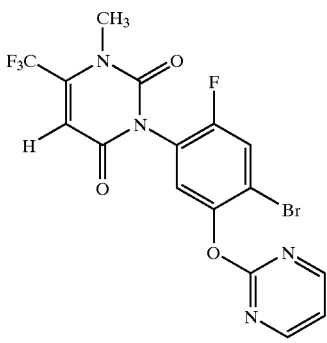

Process (e)

At room temperature, 0.46 g (3.6 mmol) of dimethyl sulphate is added dropwise with stirring to a mixture of 1.35 g (3.0 mmol) of 1-[4-bromo-2-fluoro-5-(pyrimidin-2-yl-oxy)-phenyl]-4-trifluormethyl-3,6-dihydro-2,6-dioxo-1 (2H)-pyrimidine, 0.84 g (6.0 mmol) of potassium carbonate and 25 ml of acetonitrile, and the reaction mixture is heated at reflux for 2 hours. The mixture is cooled to room temperature, diluted with water to about twice its original volume and then extracted three times with methylene chloride. The combined organic phases are dried with sodium sulphate and filtered. The filtrate is concentrated under waterpump vacuum and the residue is taken up in ethyl acetate and filtered off with suction through silica gel. The filtrate is concentrated under waterpump vacuum, the residue is digested with diethyl ether and the resulting crystalline product is isolated by filtration with suction.

This gives 0.70 g (51% of theory) of 1-[4-bromo-2-fluoro-5-(pyrimidin-2-yl-oxy)-phenyl]-3-methyl-4-trifluoromethyl-3,6-dihydro-2,6-dioxo-1 (2H)-pyrimidine.

log P=2.47[a)]

Analogously to Examples 1 and 2, and in accordance with the general description of the preparation processes according to the invention, it is also possible to prepare, for example, the compounds of the general formula (I) listed in Table 1 below.

TABLE 1

Examples of compounds of the formula (I)

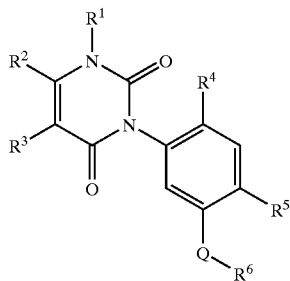

(I)

| Ex. No. | Q | $R^1$ | $R^2$ | $R^3$ | $R^4$ | $R^5$ | $R^6$ | Physical data |
|---|---|---|---|---|---|---|---|---|
| 3 | O | $CH_3$ | $CF_3$ | H | F | CN | 2-pyrimidinyl | m.p.: 96° C. |
| 4 | O | $CH_3$ | $CF_3$ | H | F | CN | 4,6-dimethoxy-pyrimidin-2-yl | m.p.: 186° C. |
| 5 | O | $CH_3$ | $CF_3$ | H | F | CN | benzoxazol-2-yl | m.p.: 143° C. |
| 6 | O | $CH_3$ | $CF_3$ | H | F | CN | 1-ethyl-pyrazol-5-yl | logP = 2.59[a)] |

TABLE 1-continued
Examples of compounds of the formula (I)
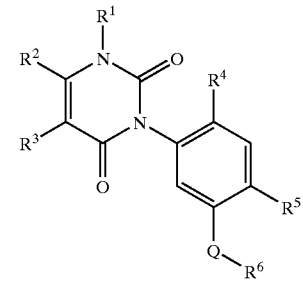
(I)
| Ex. No. | Q | R¹ | R² | R³ | R⁴ | R⁵ | R⁶ | Physical data |
|---|---|---|---|---|---|---|---|---|
| 7 | O | H | CF₃ | H | F | CN | 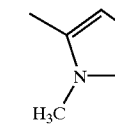 | logP = 2.03[a)] |
| 8 | O | CH₃ | CF₃ | H | F | CN | 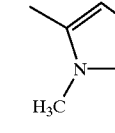 | logP = 2.50[a)] |
| 9 | O | NH₂ | CF₃ | H | F | CN | 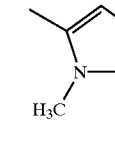 | logP = 2.21[a)] |
| 10 | O | H | CF₃ | H | F | CN | 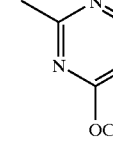 | |
| 11 | O | H | CF₃ | H | F | CN | 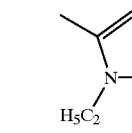 | |
| 12 | O | NH₂ | CF₃ | H | F | CN | 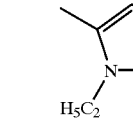 | logP = 2.32[a)] |
| 13 | O | H | CF₃ | H | F | CN | 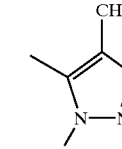 | ¹H-NMR (CD₃CN, δ): 7.75 ppm |

TABLE 1-continued

Examples of compounds of the formula (I)

| Ex. No. | Q | R¹ | R² | R³ | R⁴ | R⁵ | R⁶ | Physical data |
|---|---|---|---|---|---|---|---|---|
| 14 | O | CH₃ | CF₃ | H | F | CN | 1,3,4,5-tetramethylpyrazol-... (1,3,5-trimethyl-4-methylpyrazole group) | m.p.: 182° C. |
| 15 | O | CH₃ | CF₃ | H | F | CN | 6-chloro-4-methylpyrimidin-... | m.p.: 92° C. |
| 16 | O | CH₃ | CF₃ | H | F | CN | 6-methoxy-4-methylpyrimidin-... | |
| 17 | O | CH₃ | CF₃ | H | F | CN | 4,6-dimethylpyrimidin-... | |
| 18 | O | CH₃ | CF₃ | H | F | CN | 6-(methoxycarbonylmethoxy)-4-methylpyrimidin-... | |
| 19 | O | CH₃ | CF₃ | H | F | CN | 6-(1-methoxycarbonylethoxy)-4-methylpyrimidin-... | |

TABLE 1-continued

Examples of compounds of the formula (I)

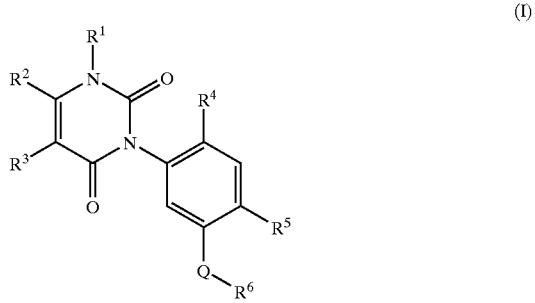

| Ex. No. | Q | $R^1$ | $R^2$ | $R^3$ | $R^4$ | $R^5$ | $R^6$ | Physical data |
|---|---|---|---|---|---|---|---|---|
| 20 | O | $CH_3$ | $CF_3$ | H | F | CN | 4-methyl-5-fluoro-6-chloropyrimidin-yl | logP = 3.08[a)] |
| 21 | O | $CH_3$ | $CF_3$ | H | F | CN | 4-methyl-5-fluoro-6-methoxypyrimidinyl | |
| 22 | O | $CH_3$ | $CF_3$ | H | F | CN | 4-methyl-5-fluoro-6-(methoxycarbonylmethoxy)pyrimidinyl | |
| 23 | O | $CH_3$ | $CF_3$ | H | F | CN | 4-methyl-5-fluoro-6-(1-methoxycarbonylethoxy)pyrimidinyl | |
| 24 | O | $CH_3$ | $CF_3$ | H | F | CN | 4-methyl-6-hydroxypyrimidinyl | |
| 25 | O | $CH_3$ | $CF_3$ | H | F | CN | 4-methyl-5-fluoro-6-hydroxypyrimidinyl | |

TABLE 1-continued

Examples of compounds of the formula (I)

(I)

[Structure: pyrimidine-2,4-dione with R¹ on N, R² and R³ on ring carbons, and N connected to phenyl ring bearing R⁴, R⁵, and O-R⁶ substituents]

| Ex. No. | Q | R¹ | R² | R³ | R⁴ | R⁵ | R⁶ | Physical data |
|---|---|---|---|---|---|---|---|---|
| 26 | O | CH₃ | CF₃ | H | F | CN | 3,5-difluoro-6-methyl-2-fluoropyridin-... (2-F, 3,5-diF, 6-Me pyridyl) | logP = 3.26[a] |
| 27 | O | CH₃ | CF₃ | H | F | CN | 3,5-difluoro-6-methyl-2-hydroxypyridyl | |
| 28 | O | CH₃ | CF₃ | H | F | CN | 3,5-difluoro-6-methyl-2-methoxypyridyl | |
| 29 | O | CH₃ | CF₃ | H | F | CN | 6-methylpyridin-2-yl | |
| 30 | O | CH₃ | CF₃ | H | F | CN | 5-methylpyridin-3-yl | logP = 2.10[a] |
| 31 | O | CH₃ | CF₃ | H | F | CN | 4-methylpyridin-... yl | |
| 32 | O | CH₃ | CF₃ | H | F | CN | 6-methyl-2-cyanopyridyl | |
| 33 | O | CH₃ | CF₃ | H | F | CN | 6-methyl-2-(trifluoromethyl)pyridyl | |
| 34 | O | CH₃ | CF₃ | H | F | CN | 5-methyl-2-chloropyridyl | |
| 35 | O | CH₃ | CF₃ | H | F | CN | 5-methyl-2-fluoropyridyl | |

TABLE 1-continued

Examples of compounds of the formula (I)

| Ex. No. | Q | R¹ | R² | R³ | R⁴ | R⁵ | R⁶ | Physical data |
|---|---|---|---|---|---|---|---|---|
| 36 | O | CH₃ | CF₃ | H | F | CN | 5-(2-trifluoromethyl)pyridyl | |
| 37 | O | H | CF₃ | H | F | CN | 1-methyl-3-n-propyl-pyrazol-5-yl | m.p.: 172° C. |
| 38 | O | NH₂ | CF₃ | H | F | CN | 1-methyl-3-n-propyl-pyrazol-5-yl | ¹H-NMR (DMSO-D₆, δ): 6.39 ppm |
| 39 | O | CH₃ | CF₃ | H | F | CN | 3,4,5-trimethyl-1H-pyrazol-5-yl | m.p.: 260° C. |
| 40 | O | NH₂ | CF₃ | H | F | Br | 2-pyrimidinyl | logP = 2.16[a] |
| 41 | O | CH₃ | CF₃ | H | F | CN | 2-methyl-3-(methoxycarbonyl)pyridyl | logP = 2.70[a] |
| 42 | O | H | CF₃ | H | F | Br | 2-methyl-3-cyanopyridyl | |
| 43 | O | H | CF₃ | H | F | Br | 4,6-dimethoxy-2-pyrimidinyl | |

TABLE 1-continued
Examples of compounds of the formula (I)
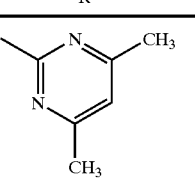
(I)
| Ex. No. | Q | R¹ | R² | R³ | R⁴ | R⁵ | R⁶ | Physical data |
|---|---|---|---|---|---|---|---|---|
| 44 | O | CH₃ | CF₃ | H | F | Br | 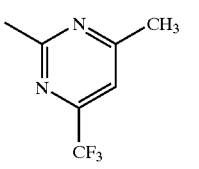 | logP = 2.84[a] |
| 45 | O | CH₃ | CF₃ | H | F | Br | 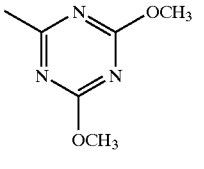 | logP = 3.59[a] |
| 46 | O | CH₃ | CF₃ | H | F | Br | 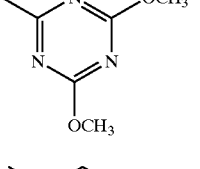 | logP = 2.93[a] |
| 47 | O | CH₃ | CF₃ | H | F | Br | 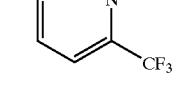 | logP = 3.48[a] |
| 48 | O | CH₃ | CF₃ | H | F | Br | 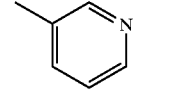 | logP = 3.83[a] |
| 49 | O | H | CF₃ | H | F | CN | 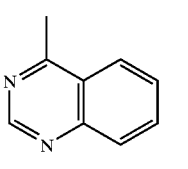 | |
| 50 | O | CH₃ | CF₃ | H | F | CN | 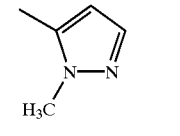 | logP = 2.41[a] |
| 51 | O | H | CF₃ | H | F | CN | | logP = 1.88[a] |

TABLE 1-continued

Examples of compounds of the formula (I)

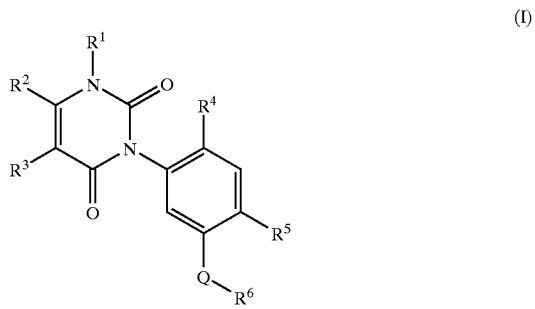

(I)

| Ex. No. | Q | R¹ | R² | R³ | R⁴ | R⁵ | R⁶ | Physical data |
|---|---|---|---|---|---|---|---|---|
| 52 | O | H | CF₃ | H | F | CN | 1-ethyl-3,5-dimethylpyrazol-4-yl | logP = 2.16[a)] |
| 53 | O | CH₃ | CF₃ | H | F | CN | 1-methyl-5-methylpyrazol-4-yl | logP = 2.33[a)] |
| 54 | O | CH₃ | CF₃ | H | F | CN | 1-ethyl-3,5-dimethylpyrazol-4-yl | logP = 2.68[a)] |
| 55 | O | CH₃ | CF₃ | H | F | CN | 1-methyl-3-trifluoromethylpyrazol-4-yl | logP = 3.26[a)] |
| 56 | O | H | CF₃ | H | F | Br | 2-methyl-5-bromopyrimidin-4-yl | |
| 57 | O | CH₃ | CF₃ | H | F | Br | 2-methyl-5-bromopyrimidin-4-yl | logP = 3.16[a)] |
| 58 | O | CH₃ | CF₃ | H | F | Br | 2,6-dimethyl-4-chloropyrimidin-5-yl | logP = 3.20[a)] |
| 59 | O | H | C(O)CH₃ (OH) | H | F | CN | 1-ethyl-5-methylpyrazol-4-yl | |

TABLE 1-continued

Examples of compounds of the formula (I)

(I)

| Ex. No. | Q | R¹ | R² | R³ | R⁴ | R⁵ | R⁶ | Physical data |
|---|---|---|---|---|---|---|---|---|
| 60 | O | CH₃ | NH₂-C(=O)-CH₃ (acetamido) | H | F | CN | 1-ethyl-5-methylpyrazol-yl | logP = 1.47[a] |
| 61 | O | H | OH-C(=O)-CH₃ (acetoxy) | H | F | CN | 1-methyl-5-methylpyrazol-yl | |
| 62 | O | H | CF₃ | H | F | Br | 2-methyl-6-methyl-4-carboxypyrimidin-yl | |
| 63 | O | CH₃ | CN | H | F | CN | 1-ethyl-5-methylpyrazol-yl | logP = 2.11[a] |
| 64 | O | CH₃ | CF₃ | H | F | Br | 2-methyl-3-cyanopyridin-yl | logP = 2.96[a] |
| 65 | O | CH₃ | CF₃ | H | F | Br | 2-methyl-6-chloro-4-(methoxycarbonyl)pyrimidin-yl | logP = 3.20[a] |
| 66 | O | H | CF₃ | H | F | Br | 6-methyl-3-cyanopyridin-yl | |
| 67 | O | NH₂ | CF₃ | H | F | CN | 2-methylpyrimidin-yl | |

TABLE 1-continued

Examples of compounds of the formula (I)

(I)

| Ex. No. | Q | $R^1$ | $R^2$ | $R^3$ | $R^4$ | $R^5$ | $R^6$ | Physical data |
|---|---|---|---|---|---|---|---|---|
| 68 | O | $CH_3$ | $CF_3$ | H | H | CN | methyl 2-methylpyridine-3-carboxylate | |
| 69 | O | $CH_3$ | $CF_3$ | H | F | CN | methyl 2-methyl-5-methylpyridine-3-carboxylate | |
| 70 | O | $CH_3$ | $CF_3$ | H | F | CN | ethyl 2-methyl-5-methylpyridine-3-carboxylate | |
| 71 | O | $CH_3$ | $CF_3$ | H | F | CN | methyl 6-methylpyridine-3-carboxylate | |
| 72 | O | $CH_3$ | $CF_3$ | H | F | CN | methyl 6-methylpyridine-2-carboxylate | |
| 73 | O | $CH_3$ | $CF_3$ | H | F | CN | methyl 2-methylpyridine-4-carboxylate | |

The log P values given in Table 1 were determined in accordance with EEC Directive 79/831 Annex V.A8 by HPLC (High Performance Liquid Chromatography) using a reversed-phase column (C18). Temperature: 43° C.

(a) Mobile phases for the determination in the acidic range: 0.1% aqueous phosphoric acid, acetonitrile; linear gradient from 10% acetonitrile to 90% acetonitrile—the corresponding test results in Table I are labelled a).

(b) Mobile phases for the determination in the neutral range: 0.01 molar aqueous phosphate buffer solution, acetonitrile; linear gradient from 10% acetonitrile to 90% acetonitrile—the corresponding test results in Table 1 are labelled b).

Calibration was carried out using unbranched alkan-2-ones (having 3 to 16 carbon atoms) with known log P values (determination of the log P values by the retention times using linear interpolation between two successive alkanones).

The lambda-max values were determined using the UV spectra from 200 nm to 400 nm in the maxima of the chromatographic signals.

The compound listed above in Table 1 as Example 4 can be prepared, for example, as follows:

Example 4

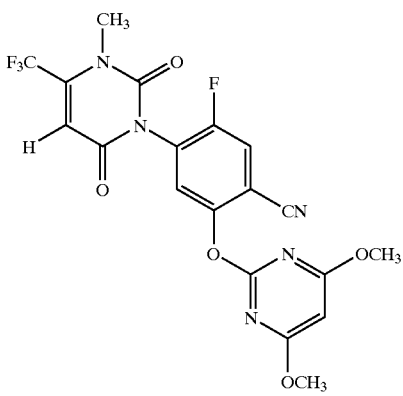

Process (a)

A mixture of 0.50 g (1.5 mmol) of 1-(4-cyano-2-fluoro-5-hydroxy-phenyl)-3-methyl-4-trifluoromethyl-3,6-dihydro-2,6-dioxo-1(2H)-pyrimidine, 0.30 g (2.2 mmol) of potassium carbonate and 50 ml of dimethyl sulphoxide is stirred at room temperature (about 20° C.) for 15 minutes. 0.36 g (1.7 mmol) of 4,6-dimethoxy-2-methyl-sulphonyl-pyrimidine is added, and the reaction mixture is then stirred at 60° C. for 3 hours, then at 90° C. for 8 hours, at room temperature for a further 12 hours, at 90° C. for a further 12 hours and finally at room temperature for a further 12 hours. The mixture is then poured into a saturated aqueous solution of sodium chloride and extracted with ethyl acetate, and the organic phase is washed with water and then with saturated aqueous sodium chloride solution, dried with sodium sulphate and filtered. The filtrate is concentrated under waterpump vacuum, the residue is digested with diethyl ethyl/diisopropyl ether and the resulting crystalline product is isolated by filtration with suction.

This gives 0.20 g (29% of theory) of 1-[4-cyano-2-fluoro-5-(4,6-dimethoxy-pyrimidin-2-yl-oxy)-phenyl]-3-methyl-4-trifluoromethyl-3,6-dihydro-2,6-dioxo-1(2H)-pyrimidine of melting point 186° C.

Starting Materials of the Formula (VIII)

Example (VIII-1)

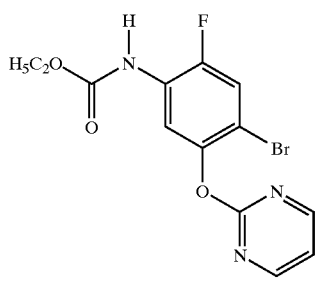

2.0 g (7.0 mmol) of 4-bromo-2-fluoro-5-(pyrimidin-2-yl-oxy)-aniline are initially charged in 25 ml of methylene chloride and, at room temperature (about 20° C.), admixed with 0.92 g (8.4 mmol) of ethyl chloroformate and then with 0.67 g (8.4 mmol) of pyridine. The reaction mixture is then stirred at room temperature for 4 hours. The mixture is subsequently diluted with 2N hydrochloric acid to about twice its original volume and extracted with methylene chloride. The organic phase is dried with sodium sulphate and filtered. The filtrate is concentrated under waterpump vacuum, the residue is digested with diethyl ether and the resulting crystalline product is isolated by filtration with suction.

This gives 2.2 g (89% of theory) of O-ethyl N-[4-bromo-2-fluoro-5-(pyrimidin-2-yl-oxy)-phenyl]-carbamate of melting point 178° C.

Analogously to Example (VIII-1), it is also possible to prepare, for example, the compounds of the general formula (VIII) listed in Table 2 below.

(VIII)

TABLE 2

| Ex. No. | Q | $R^4$ | $R^5$ | $R^6$ | R | Physical data |
|---|---|---|---|---|---|---|
| VIII-2 | O | F | CN | 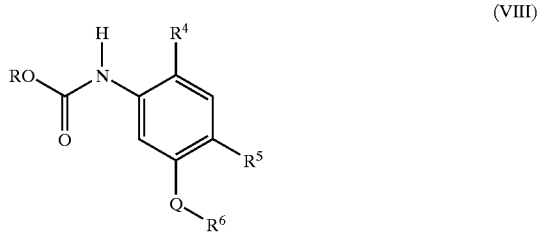 | $C_2H_5$ | logP = 2.19[a)] |
| VIII-3 | O | F | Br | | $C_2H_5$ | |

TABLE 2-continued

Examples of compounds of the formula (VIII)

| Ex. No. | Q | $R^4$ | $R^5$ | $R^6$ | R | Physical data |
|---|---|---|---|---|---|---|
| VIII-4 | O | F | CN | 5-methyl-1-methyl-pyrazol-3-yl | $C_2H_5$ | |
| VIII-5 | O | F | CN | 1-ethyl-pyrazol-3-yl | $C_2H_5$ | m.p.: 158° C. |
| VIII-6 | O | F | CN | 3,5-dimethyl-1-ethyl-pyrazol-4-yl (3-CH₃, 5-CH₃, N-C₂H₅) | $C_2H_5$ | |
| VIII-7 | O | F | CN | 3,4,5-trimethyl-1-methyl-pyrazolyl | $C_2H_5$ | |
| VIII-8 | O | F | CN | 3-CF₃-1-methyl-pyrazol-5-yl | $C_2H_5$ | |
| VIII-9 | O | F | CN | 1-propyl-pyrazol-3-yl | $C_2H_5$ | |
| VIII-10 | O | F | CN | 4,6-dimethyl-pyrimidin-2-yl | $C_2H_5$ | |
| VIII-11 | O | F | CN | 2-OCH₃-3,5-difluoro-pyridin-6-yl | $C_2H_5$ | |
| VIII-12 | O | F | CN | pyridin-2-yl | $C_2H_5$ | |
| VIII-13 | O | F | CN | pyridin-3-yl | $C_2H_5$ | |
| VIII-14 | O | F | CN | pyridin-4-yl | $C_2H_5$ | |
| VIII-15 | O | F | CN | 4,6-dimethyl-pyrimidin-2-yl (6-CH₃) | $C_2H_5$ | |
| VIII-16 | O | F | CN | 4-methyl-6-CF₃-pyrimidin-2-yl | $C_2H_5$ | |

Use Examples

Example A

Pre-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is sprayed with the preparation of active compound such that the particular amount of active compound desired is applied per unit area. The concentration of active compound in the spray liquor is chosen such that the particular amount of active compound desired is applied in 1000 liters of water per hectare.

After three weeks, the degree of damage to the plants is rated in % damage in comparison to the development of the untreated control. The figures denote:

0%=no effect (like untreated control)

100%=total destruction

In this test, for example, the compounds of Preparation Examples 2 and 6 exhibit very strong activity against weeds.

Example B

Post-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The Figures Denote

0%=no effect (like untreated control)
100%=total destruction

In this test, for example, the compounds of Preparation Examples 2 and 6 exhibit very strong activity against weeds.

What is claimed is:

1. A member selected from the group consisting of a substituted phenyluracil compound of the Formula (I)

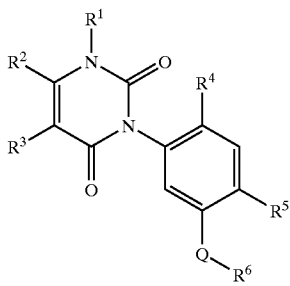

wherein
Q represents O, S, SO or $SO_2$,
$R^1$ represents hydrogen, amino, optionally cyano-, halogen- or $C_1$–$C_4$-alkoxy-substituted alkyl having 1 to 4 carbon atoms or in each case optionally halogen-substituted alkenyl or alkinyl having in each case 2 to 4 carbon atoms,
$R^2$ represents cyano, carboxyl, carbamoyl, thiocarbamoyl or in each case optionally cyano-, halogen- or $C_1$–$C_4$-alkoxy-substituted alkyl or alkoxy-carbonyl having in each case 1 to 4 carbon atoms,
$R^3$ represents hydrogen, halogen or optionally halogen-substituted alkyl having 1 to 4 carbon atoms,
$R^4$ represents hydrogen, nitro, cyano or halogen,
$R^5$ represents cyano, thiocarbamoyl, bromine or in each case optionally halogen-substituted alkyl or alkoxy having in each case 1 to 4 carbon atoms, and
$R^6$ represents an optionally nitro-, hydroxyl-, mercapto-, amino-, cyano-, carboxyl-, carbamoyl-, halogen-, $C_1$–$C_4$-alkyl-, cyano-$C_1$–$C_4$-alkyl-, carboxyl-$C_1$–$C_4$-alkyl-, $C_1$–$C_4$-halogenoalkyl-, $C_1$–$C_4$-alkoxy-$C_1$–$C_4$-alkyl-, $C_1$–$C_4$-alkoxy-carbonyl-$C_1$–$C_4$-alkyl-, $C_1$–$C_4$-alkylaminocarbonylalkyl-, di-($C_1$–$C_4$-alkyl)-aminocarbonylalkyl-, $C_1$–$C_4$-alkoxy-, cyano-$C_1$–$C_4$-alkoxy-, $C_1$–$C_4$-halogenoalkoxy-, $C_1$–$C_4$-alkoxy-$C_1$–$C_4$-alkoxy-, carboxyl-$C_1$–$C_4$-alkoxy-, $C_1$–$C_4$-alkoxy-carbonyl-$C_1$–$C_4$-alkoxy-, $C_1$–$C_4$-alkylamino-carbonyl-$C_1$–$C_4$-alkoxy, di-($C_1$–$C_4$-alkyl)-aminocarbonyl-$C_1$–$C_4$-alkoxy-, $C_1$–$C_4$-alkoxy-carbonyl-, $C_2$–$C_4$-alkenyloxy-, $C_2$–$C_4$-alkinyloxy-, $C_1$–$C_4$-alkylthio-, $C_1$–$C_4$-halogenoalkylthio, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, $C_1$$C_4$-alkyl-carbonyl-amino-, $C_1$–$C_4$-alkoxy-carbonyl-amino- or $C_1$–$C_4$-alkyl-sulphonyl-amino-substituted nitrogen-containing heterocyclic grouping selected from the group consisting of pyrrolyl, pyrazolyl, imidazolyl, triazolyl, triazolinyl, pyridinyl, pyrazinyl, pyridazinyl, pyrimidinyl, triazinyl, benzoxazolyl, benzothiazolyl, quinolinyl, quinazolinyl, and quinoxalinyl, one or more tautomeric forms of the compound of the Formula (I), one or more salts of the compound of the Formula (I), one or more acid adducts of the compound of the Formula (I), one or more base adducts of the compound of the Formula (I) and combinations thereof.

2. The compound according to claim 1, wherein
Q represents O, S or $SO_2$,
$R^1$ represents hydrogen, amino, in each case optionally cyano-, fluorine-, chlorine-, methoxy- or ethoxy-substituted methyl, ethyl, n- or i-propyl, or in each case optionally fluorine- and/or chlorine-substituted propenyl or propinyl,
$R^2$ represents cyano, carboxyl, carbamoyl, thiocarbamoyl or in each case optionally cyano-, fluorine-, chlorine-, methoxy- or ethoxy-substituted methyl, ethyl, n- or i-propyl, methoxycarbonyl, ethoxycarbonyl, n- or i-propoxycarbonyl,
$R^3$ represents hydrogen, fluorine, chlorine, bromine or in each case optionally fluorine- and/or chlorine-substituted methyl, ethyl, n- or i-propyl,
$R^4$ represents hydrogen, cyano, fluorine, chlorine or bromine,
$R^5$ represents cyano, thiocarbamoyl, bromine or in each case optionally fluorine- and/or chlorine-substituted methyl, ethyl, methoxy or ethoxy, and
$R^6$ represents an in each case optionally nitro-, hydroxyl-, amino-, cyano-, carboxyl-, carbamoyl-, fluorine-, chlorine-, bromine-, methyl-, ethyl-, n- or i-propyl-, n-, i-, s- or t-butyl-, chloromethyl-, fluoromethyl-, dichloromethyl-, difluoromethyl-, trichloromethyl-, trifluoromethyl-, chlorodifluoromethyl-, fluorodichloromethyl-, chloroethyl-, fluoroethyl-, dichloroethyl-, difluoroethyl, chlorofluoroethyl-, trichloroethyl-, trifluoroethyl-, chlorodifluoroethyl-, fluorodichloroethyl-, tetrafluoroethyl-, chlorotrifluoroethyl-, pentafluoroethyl-, chloro-n-propyl-, fluoro-n-propyl-, chloro-i-propyl-, fluoro-i-propyl-, dichloropropyl-, difluoropropyl-, trichloropropyl-, trifluoropropyl-, cyanomethyl-, cyanoethyl-, cyanopropyl-, carboxymethyl-, carboxyethyl-, carboxypropyl-, methoxymethyl-, ethoxymethyl-, propoxymethyl-, methoxyethyl-, ethoxyethyl-, methoxycarbonyl methyl-, ethoxycarbonyl methyl-, n- or i-propoxycarbonylmethylmethylaminocarbonylmethyl-, ethylaminocarbonylmethyl-, dimethylaminocarbonylmethyl-, methoxycarbonylethyl-, ethoxycarbonylethyl-, n- or i-propoxycarbonylethyl-, methoxy-, ethoxy-, n- or i-propoxy-, n-, i-, s- or t-butoxy-, difluoromethoxy-, trifluoromethoxy-, chlorodifluoromethoxy-, carboxymethoxy-, carboxyethoxy-, methoxycarbonyl methoxy-, ethoxycarbonylmethoxy-, n- or i-propoxycarbonylmethoxy-, methylaminocarbonylmethoxy-, ethylaminocarbonylmethoxy-, dimethylaminocarbonylmethoxy-, methoxycarbonylethoxy-, ethoxycarbonylethoxy-, n- or i-propoxycarbonylethoxy-, methylaminocarbonylethoxy-, ethylaminocarbonylethoxy-, dimethylaminocarbonylethoxy-, methoxycarbonyl-, ethoxycarbonyl-, n- or 1-propoxycarbonyl-, propenyloxy-, butenyloxy-, propinyloxy-, butinyloxy-, methylthio-, ethylthio-, n- or i-propylthio-, n-, i-, s- or t-butylthio-, difluoromethylthio-, trifluoromethylthio-, chlorodifluoromethylthio-, methylsulphinyl-, ethylsulphinyl-, n- or i-propylsulphinyl-, trifluoromethylsulphinyl-, methylsulphonyl-, ethylsulphonyl-, n- or i-propylsulfonyl-, trifluoromethylsulphonyl-, acetylamino-, propionylamino-, n- or i-butyroylamino-, methoxycarbonylamino-, ethoxycarbonylamino-, n- or i-propoxycarbonylamino-, methylsulphonylamino-, ethylsulphonylamino-, n- or i-propylsulphonylamino-substituted nitrogen-containing heterocyclic grouping selected from the group consisting of pyrrolyl, pyrazolyl, imidazolyl, triazolyl, triazolinyl, pyridinyl, pyrazinyl, pyridazinyl, pyrimidinyl, triazinyl, benzoxazolyl, benzothiazolyl, quinolinyl, quinazolinyl, and quinoxalinyl.

3. The compound according to claim 1 wherein

Q represents O or S, $R^1$ represents hydrogen, amino or represents in each case optionally fluorine-, chlorine-, methoxy- or ethoxy-substituted methyl or ethyl, $R^2$ represents cyano, carboxyl, carbamoyl or in each case optionally fluorine- and/or chlorine-substituted methyl, ethyl, methoxycarbonyl or ethoxycarbonyl, $R^3$ represents hydrogen, fluorine, chlorine, bromine or in each case optionally fluorine- and/or chlorine-substituted methyl or ethyl, $R^4$ represents hydrogen, fluorine or chlorine, $R^5$ represents cyano, thiocarbamoyl, bromine or trifluoromethyl, and $R^6$ represents an in each case optionally nitro-, hydroxyl-, amino-, cyano-, carboxyl-, carbamoyl-, fluorine-, chlorine-, bromine-, methyl-, ethyl-, n- or i-propyl-, n-, i-, s- or t-butyl-, dichloromethyl-, difluoromethyl-, trichloromethyl-, trifluoromethyl-, chlorodifluoromethyl-, fluorodichloromethyl-, methoxy-, ethoxy-, n- or i-propoxy-, n-, i-, s- or t-butoxy-, di-fluoromethoxy-, trifluoromethoxy-, chlorodifluoromethoxy-, carboxy-methoxy-, carboxyethoxy-, methoxycarbonyl methoxy-, ethoxycarbonylmethoxy-, n- or i-propoxycarbonylmethoxy-, methoxycarbonylethoxy-, ethoxycarbonylethoxy-, n- or i-propoxycarbonylethoxy-, methoxycarbonyl-, ethoxycarbonyl-, propenyloxy-, butenyloxy-, propinyloxy-, butinyloxy-, methylthio-, ethylthio-, n- or i-propylthio-, n-, i-, s- or t-butyl-thio-, difluoromethylthio-, trifluoromethylthio-, chlorodifluoromethylthio-, methylsulphinyl-, ethylsulphinyl-, n- or i-propylsulphinyl-, trifluoromethylsulphinyl-, methylsulphonyl, ethylsulphonyl-, n- or i-propylsulphonyl-, trifluoromethylsulphonyl-, acetylamino-, propionylamino-, n- or i-butyroylamino-, methoxycarbonylamino-, ethoxycarbonylamino-, n- or i-propoxycarbonylamino-, methylsulphonylamino-, ethylsulphonylamino-, n- or i-propylsulphonylamino-substituted nitrogen-containing heterocyclic grouping selected from the group consisting of pyrrolyl, pyrazolyl, imidazolyl, triazolyl, triazolinyl, pyridinyl, pyrazinyl, pyridazinyl, pyrimidinyl, triazinyl, benzoxazolyl, benzothiazolyl, quinolinyl, quinazolinyl, and quinoxalinyl.

4. The compound according to claim 1 wherein $R^1$ represents hydrogen, amino, methyl or ethyl, $R^2$ represents cyano or trifluoromethyl, $R^3$ represents hydrogen, chlorine or methyl, $R^5$ represents cyano, thiocarbamoyl or bromine, and $R^6$ represents in each case optionally hydroxyl-, amino-, cyano-, carboxyl-, carbamoyl-, fluorine-, chlorine-, bromine-, methyl-, ethyl-, n- or i-propyl-, n-, i-, s- or t-butyl-, dichloromethyl-, difluoromethyl-, trichloromethyl-, trifluoromethyl-, chlorodifluoromethyl-, fluorodichloromethyl-, methoxy-, ethoxy-, n- or i-propoxy-, difluoromethoxy-, trifluoromethoxy-, chlorodifluoromethoxy-, carboxymethoxy-, carboxyethoxy-, methoxycarbonylmethoxy-, ethoxycarbonylmethoxy-, n- or i-propoxycarbonylmethoxy-, methoxycarbonylethoxy-, ethoxycarbonylethoxy-, n- or i-propoxycarbonylethoxy-, methoxycarbonyl-, ethoxycarbonyl-, propenyloxy-, butenyloxy-, propinyloxy-, butinyloxy-, methylthio-, ethylthio-, n- or i-propylthio-, difluoromethylthio-, trifluoromethylthio-, chlorodifluoromethylthio-, methylsulphinyl-, ethylsulphinyl-, n- or i-propylsulphinyl-, trifluoromethylsulphinyl-, methylsulphonyl-, ethylsulphonyl-, n- or i-propylsulfonyl-, trifluoromethylsulphonyl-, acetylamino-, propionylamino-, n- or i-butyroylamino-, methoxycarbonylamino-, ethoxycarbonylamino-, n- or i-propoxycarbonylamino-, methylsulphonylamino-, ethylsulphonylamino-, n- or i-propylsulphonylamino-substituted pyrazolyl, pyridinyl, pyrimidinyl, triazinyl or benzoxazolyl.

5. The compound according to claim 1 wherein $R^1$ represents hydrogen, amino or methyl, $R^2$ represents trifluoromethyl, $R^5$ represents cyano or bromine, and $R^6$ represents in each case optionally hydroxyl-, amino-, cyano-, fluorine-, chlorine-, methyl-, ethyl-, trichloromethyl-, methoxy- or ethoxy-substituted pyrazolyl, pyridinyl, pyrimidinyl or benzoxazolyl.

6. The compound according to claim 1 wherein

Q represents O.

* * * * *